(12) United States Patent
Benecke et al.

(10) Patent No.: US 9,302,976 B2
(45) Date of Patent: Apr. 5, 2016

(54) BIO-POLYOLS FOR BIO-LUBRICANT AND BIO-POLYMER AND METHODS FOR THE PREPARATION THEREOF

(71) Applicant: PETROLIAM NASIONAL BERHAD, Kuala Lumpur (MY)

(72) Inventors: Herman Paul Benecke, Columbus, OH (US); Daniel B. Garbark, Blacklick, OH (US)

(73) Assignee: Petroliam Nasional Berhad, Kuala Lumpur (MY)

( * ) Notice: Subject to any disclaimer, the term of this patent is extended or adjusted under 35 U.S.C. 154(b) by 0 days.

(21) Appl. No.: 14/381,564

(22) PCT Filed: Feb. 28, 2013

(86) PCT No.: PCT/MY2013/000042
§ 371 (c)(1),
(2) Date: Aug. 27, 2014

(87) PCT Pub. No.: WO2013/129911
PCT Pub. Date: Sep. 6, 2013

(65) Prior Publication Data
US 2015/0087850 A1   Mar. 26, 2015

Related U.S. Application Data

(60) Provisional application No. 61/604,165, filed on Feb. 28, 2012.

(51) Int. Cl.
C07C 67/02 (2006.01)
C07C 67/03 (2006.01)
C07C 67/39 (2006.01)
C11C 1/00 (2006.01)
C11C 1/04 (2006.01)
C11C 3/00 (2006.01)
(Continued)

(52) U.S. Cl.
CPC .............. *C07C 67/02* (2013.01); *C07C 51/09* (2013.01); *C07C 67/00* (2013.01); *C07C 67/03* (2013.01); *C07C 67/08* (2013.01); *C07C 67/39* (2013.01); *C11C 1/005* (2013.01); *C11C 1/04* (2013.01); *C11C 3/00* (2013.01); *C11C 3/003* (2013.01); *C11C 3/006* (2013.01); *C11C 3/02* (2013.01)

(58) Field of Classification Search
None
See application file for complete search history.

(56) References Cited

U.S. PATENT DOCUMENTS 667,043  A   1/1901  Steep
2,401,338 A  6/1946  Dunmire
(Continued)

FOREIGN PATENT DOCUMENTS

AU  165032      2/1954
CN  102010772 A 4/2011
(Continued)

OTHER PUBLICATIONS

International Search Report and Written Opinion for PCT/MY2013/000042 mailed Jun. 28, 2013.
(Continued)

*Primary Examiner* — Yate K Cutliff
(74) *Attorney, Agent, or Firm* — LeClairRyan, a Professional Corporation

(57) ABSTRACT

A method for producing an ester polyol, comprising transesterifying a first ester polyol with a primary polyol to produce a second ester polyol, wherein the second ester polyol has a higher hydroxyl value than the first ester polyol.

26 Claims, 6 Drawing Sheets

Overall Master Batch Method $HV > HV_i$

(51) Int. Cl.
  *C11C 3/02* (2006.01)
  *C07C 51/09* (2006.01)
  *C07C 67/00* (2006.01)
  *C07C 67/08* (2006.01)

(56) References Cited

U.S. PATENT DOCUMENTS

| | | | |
|---|---|---|---|
| 2,566,559 A | 9/1951 | Dolnick et al. | |
| 2,813,113 A | 11/1957 | Goebel et al. | |
| 2,997,493 A | 8/1961 | Huber | |
| 4,061,581 A | 12/1977 | Leleu et al. | |
| 4,298,730 A | 11/1981 | Galleymore et al. | |
| 4,313,890 A | 2/1982 | Chu et al. | |
| 5,773,256 A | 6/1998 | Pelenc et al. | |
| 5,773,391 A | 6/1998 | Lawate et al. | |
| 6,107,500 A | 8/2000 | Prossel et al. | |
| 7,125,950 B2 | 10/2006 | Dwan'Isa et al. | |
| 7,192,457 B2* | 3/2007 | Murphy et al. | 44/275 |
| 7,589,222 B2 | 9/2009 | Narayan et al. | |
| 2004/0167343 A1* | 8/2004 | Halpern et al. | 554/176 |
| 2005/0112267 A1 | 5/2005 | Kian et al. | |
| 2006/0194974 A1 | 8/2006 | Narayan et al. | |
| 2009/0216040 A1 | 8/2009 | Benecke et al. | |
| 2010/0087350 A1 | 4/2010 | Sonnenschein et al. | |
| 2010/0117022 A1 | 5/2010 | Carr et al. | |
| 2011/0269979 A1 | 11/2011 | Benecke et al. | |
| 2011/0269981 A1 | 11/2011 | Benecke et al. | |
| 2011/0269982 A1 | 11/2011 | Benecke et al. | |
| 2012/0184758 A1* | 7/2012 | Krull et al. | 554/167 |
| 2015/0005520 A1 | 1/2015 | Benecke et al. | |
| 2015/0018260 A1 | 1/2015 | Benecke et al. | |
| 2015/0018444 A1 | 1/2015 | Garbark et al. | |
| 2015/0080599 A1 | 3/2015 | Garbark et al. | |

FOREIGN PATENT DOCUMENTS

| | | |
|---|---|---|
| EP | 0010333 A1 | 4/1980 |
| EP | 1260497 A2 | 11/2002 |
| EP | 1529828 A1 | 5/2005 |
| EP | 1533360 A1 | 5/2005 |
| KR | 10-2008-0023290 A | 3/2008 |
| MY | 140833 A | 1/2010 |
| WO | 9324585 A1 | 12/1993 |
| WO | 0039068 A1 | 7/2000 |
| WO | 2006-093874 A2 | 9/2006 |
| WO | 2006093874 A2 | 9/2006 |
| WO | 2007-027223 A2 | 3/2007 |
| WO | 2007027223 A2 | 3/2007 |
| WO | 2010-078505 A1 | 7/2010 |
| WO | 2010/085545 A1 | 7/2010 |
| WO | 2010078491 A1 | 7/2010 |
| WO | 2010078493 A1 | 7/2010 |
| WO | 2010078498 A1 | 7/2010 |
| WO | 2010078505 A1 | 7/2010 |
| WO | 2013129907 A1 | 9/2013 |
| WO | 2013129908 A1 | 9/2013 |
| WO | 2013129909 A1 | 9/2013 |
| WO | 2013129910 A1 | 9/2013 |
| WO | 2013129911 A1 | 9/2013 |
| WO | 2014133380 A8 | 9/2014 |

OTHER PUBLICATIONS

Ackman et al., "Ozonolysis of Unsaturated Fatty Acids. I. Ozonolysis of Oleic Acid," Can. J. Chem., 39:1956-1963 (1961).
Yunus et al., "Preparation and Characterization of Trimethylolpropane Esters from Palm Kernel Oil Methyl Esters," J. Oil Palm Research, 15(2):42-49 (2003).
Spyros, A., "Quantitative Determination of the Distribution of Free Hydroxylic and Carboxylic Groups in Unsaturated Polyester and Alkyd Resins by 31 P-NMR Spectroscopy," J. Appl. Polym. Sci., 83:1635-1642 (2002).
PCT International Search Report and Written Opinion for International Patent Application No. PCT/MY2013/000038 (Jun. 27, 2013).
PCT International Search Report and Written Opinion for International Patent Application No. PCT/MY2013/000039 (Jun. 27, 2013).
PCT International Search Report and Written Opinion for International Patent Application No. PCT/MY2013/000040 (Jun. 28, 2013).
PCT International Search Report and Written Opinion for International Patent Application No. PCT/MY2013/000041 (Jun. 28, 2013).
PCT International Search Report and Written Opinion for International Patent Application No. PCT/MY2013/000042 (Jun. 28, 2013).
International Preliminary Report on Patentability for International Patent Application No. PCT/MY2013/000038 (Sep. 12, 2014).
International Preliminary Report on Patentability for International Patent Application No. PCT/MY2013/000039 (Sep. 12, 2014).
International Preliminary Report on Patentability for International Patent Application No. PCT/MY2013/000040 (Sep. 12, 2014).
International Preliminary Report on Patentability for International Patent Application No. PCT/MY2013/000041 (Sep. 12, 2014).
International Preliminary Report on Patentability for International Patent Application No. PCT/MY2013/000042 (Sep. 12, 2014).
Third Party Submission for U.S. Appl. No. 14/381,554 dated Jul. 13, 2015.
Extended European Search Report for EP13755362.4 dated Aug. 21, 2015.
Extended European Search Report for EP13754711.3 dated Sep. 3, 2015.
PCT International Search Report and Written Opinion corresponding to PCT/MY2014/000026, filed Feb. 28, 2014 (mailed May 21, 2014).
Akerman et al., "Biolubricant Synthesis Using Immobilised Lipase: Process Optimisation of Trimethylolpropane Oleate Production," Process Biochem. 46:2225-2231 (2011).
Translated Office Action for Chinese Application No. 201380022561.5, mailed Sep. 6, 2015.
Search Report and Written Opinion for corresponding Singapore Application No. 11201405261T, mailed Sep. 10, 2015.
Search Report and Written Opinion for Singapore Application No. 11201405268P, mailed Oct. 1, 2015.
Office Action for U.S. Appl. No. 14/381,530 dated Dec. 10, 2015.
Gmehling et al., "Azeotropic Data For Binary Mixtures", Handbook of Chemistry and Physics (96th Edition, 2015-2016), pp. 6-210 to 6-228.

* cited by examiner

Figure 3: The pre-esterification of glycerin

US 9,302,976 B2

BIO-POLYOLS FOR BIO-LUBRICANT AND BIO-POLYMER AND METHODS FOR THE PREPARATION THEREOF

This application is a national stage application under 35 U.S.C. 371 from PCT/MY2013/000042, filed Feb. 28, 2013, which claims the benefit of U.S. Provisional Patent Application Ser. No. 61/604,165, filed Feb. 28, 2012, each of which is hereby incorporated by reference in its entirety.

FIELD OF THE INVENTION

The present invention relates to methods for the preparation of polyols, in particular ester polyols.

BACKGROUND OF THE INVENTION

Ester alcohols, in particular, ester polyols are very useful for the production of polyurethane-based coatings and foams, polyester applications, and lubricants. The present invention provides a process using renewable resources, such as, oils and fats, fatty acids, and fatty acid esters derived from plants and animals to produce polyurethane foams, coatings and lubricants. Chemicals derived from plants and animal fats are oleochemicals. Oleochemicals are analogous to petrochemicals, which are chemicals derived from petroleum. As the price in crude oil increases, there will be an increased demand for oleochemical-based substances.

Polyols are a class of alcohols having at least two or more hydroxyl groups. An ester is a compound derived by reacting carboxylic acids with a hydroxyl-containing compounds such as alcohols or phenols. Esters involved in the current invention are formed by condensing an acid with an alcohol.

One class of biobased lubricants are polyol esters which are formed by full esterification of all available hydroxyl groups of a polyol with fatty acids. For example, the polyol ester trimethylolpropane (TMP) trioleate, is prepared by the esterification of the polyol TMP with various grades of oleic acid. TMP trioleate contains the unsaturated oleic acid that provides lower pour points compared to the typical long chain saturated fatty acid esters. TMP trioleate is a common biobased lubricant currently available on the market.

Ester polyols are a class of compounds consisting of internal ester groups and pendant hydroxyl groups that are provided by primary polyols (a compound containing two or more hydroxyl groups). Ester polyols and their preparation are described in WO2007027223 and WO20102012078505. One of the disadvantages of some of the ester polyols used in lubricants is that their crystallization temperature is relatively high. Ester polyols prepared from feedstock with high amounts of saturated fatty acids (e.g. palmitic, stearic) may undergo phase separation, leading to two or more phases which are difficult to process into useful products.

Accordingly, there still is a need in this technical field for improved methods for the preparation of ester polyols.

SUMMARY OF THE INVENTION

The present invention of an improved method for preparing ester polyols suitable for a range of applications may address the problems in the art.

Accordingly, in one aspect the present invention is provided a method for preparing ester polyols comprising transesterifying a first ester polyol with a primary polyol to produce a second ester polyol, the second ester polyol having a hydroxyl value (HV) which is greater than a hydroxyl value ($HV_i$) of the first ester polyol.

In one particular aspect of the invention, the first ester polyol may be prepared by the sequential steps of:
  reacting a fatty acid distillate with ozone in the presence of a reactant and a catalyst to produce a reaction mixture, wherein the ozone may comprise at least two moles of ozone per carbon-to-carbon double bond of the fatty acid distillate; and
  refluxing the reaction mixture to produce the first ester polyol having a hydroxyl value ($HV_i$). The fatty acid distillate may be a palm fatty acid distillate. The reactant may be a solvent. In particular, the solvent may be selected from ethyl acetate, methyl acetate, ethyl propionate, methyl propionate, ethyl butyrate, methyl butyrate, ethyl isobutyrate, butyl acetate, butyl butyrate, isobutyl isobutyrate, or a mixture thereof. The catalyst may be an acid catalyst. The hydroxyl value of the second ester polyol may be greater than about 300.

In one particular aspect of the invention, the first ester polyol may be prepared by the sequential steps of:
  hydrolyzing a triglyceride to produce at a mixture of fatty acids;
  esterifying the mixture of fatty acids with at least one monoalcohol to form at least one fatty acid alkyl ester;
  performing fractionation by distillation of the at least one fatty alkyl acid ester to partially remove saturates;
  reacting the at least one fractionated fatty alkyl acid ester with ozone to produce a mixture of ozone esters, wherein the ozone comprises one mole of ozone per carbon-to-carbon double bond of the at least one fractionated fatty alkyl acid ester; and
  transesterifying the mixture of ozone esters with a primary polyol to produce the first ester polyol having a hydroxyl value ($HV_i$). The at least one monoalcohol may comprise 1-butanol or isomers thereof, 1-pentanol or isomers thereof, 1-hexanol or isomers thereof, 1-heptanol or isomers thereof, 1-octanol or isomers thereof, 1-nonanol or isomers thereof, 1-decanol or isomers thereof, 1-undecanol or isomers thereof, 1-dodecanol or isomers thereof, 1-tridecanol or isomers, 1-tetradecanol or isomers thereof, cetyl alcohol or isomers, or stearyl alcohol or isomers thereof. The saturates may comprise palmitic and/or stearic esters. The triglyceride may be selected from palm oil, olein, palm fatty acid distillate (PFAD) or palm kernel fatty acid distillate (PKFAD). The hydroxyl value of the second ester polyol may be greater than about 316. The transesterifying the mixture of ozone esters and the first ester polyol may be in the presence of a tin catalyst. The second ester polyol may have an acid value (AV) of less than about 0.9.

In one particular aspect of the invention, the first ester polyol may be prepared by the sequential steps of:
  reacting a substance having at least one carbon-to-carbon double bond with ozone in the presence of at least one monoalcohol that azeotropes with water and at least one solvent to produce a plurality of ozone esters, wherein the ozone comprises at least one first mole of ozone and at least one second mole of ozone and wherein the reacting step comprises refluxing the substance having the at least one carbon-to-carbon double bond before adding the second mole of ozone; and
  transesterifying the plurality of ozone esters with a primary polyol to produce the first ester polyol having a hydroxyl value ($HV_i$). The at least one solvent may comprise at least one solvent that azeotropes with water. In particular, the at least one solvent that azeotropes with water may be selected from ethyl acetate, methyl acetate, ethyl propionate, methyl propionate, ethyl butyrate, methyl butyrate, ethyl isobutyrate, butyl acetate, butyl butyrate, isobutyl isobutyrate, or a mixture thereof. The reacting step may further comprise an acid catalyst. The at least one monoalcohol that azeotropes with water may form an azeotrope composition, and the azeotrope composition may have a water content from a range of 4 to 90 percent water. The reacting step may comprise reacting the substance having at least one carbon-to-carbon double bond in the presence of an ozonolysis catalyst. The substance having at least one carbon-to-carbon double bond may comprise a vegetable oil and/or animal fat. The substance having at least one carbon-to-carbon double bond may comprise a fatty acid. The substance having at least one carbon-to-carbon double bond may comprise a fatty acid ester.

According to any aspect of the invention, the primary polyol may be selected from glycerin, trimethylolpropane, pentaerythritol, 1,2-propylene glycol, 1,3-propylene glycol, 2-methyl-1,3-propanediol, 1,4-butanediol, ethylene glycol, glucitol fructose, glucose, sucrose, aldoses, ketoses, alditols, disaccharides, or combinations thereof Specific polyol esters of the present invention can easily be reacted with additional primary polyols to increase their hydroxyl values. Further, their preparation process simplifies the overall polyol synthesis. Polyols of different composition and characteristics have been made by the transesterification of one parent polyol or master batch. One advantage of this process is that the master batch polyol could be made continuously and then the product polyol can be tailored to the desired specification. Therefore, from one main polyol composition, the master batch, a family of polyols may be created for different end use applications. This increases efficiency and decreases processing costs.

The master batch approach for producing ester polyols can be applied to at least three areas. In each application, a low hydroxyl value (HV) polyol is transesterified with a primary polyol or polyols to produce an ester polyol with a higher hydroxyl value (HV). Rigid foam polyols and coatings polyols can be produced from the transesterification of a low hydroxyl value polyol with a primary polyol or polyols from a parent or master batch of flexible foam ester polyols having a lower hydroxyl value than the target ester polyols. The specific application will depend on the amount of primary polyol.

The low hydroxyl value polyols are capped with carboxylic acids and esterified with mixtures of primary polyols. The resulting polyols contain the properties necessary for rigid foam and coatings.

In an aspect of the present invention, a low hydroxyl value ester polyol undergoes an ozonolysis reaction resulting in non-desired oxidation of primary hydroxyl groups to form carboxylic acid groups in combination with a reduced quantity of desired hydroxyl groups. Accordingly, this material was subjected to esterification and transesterification with variable ratios of primary polyol to achieve ester polyols with greatly reduced acid values that produced both flexible and rigid foams with greatly reduced acid values and properties comparable to those obtained by standard processes. Thus, the Master Batch approach can also be successfully applied to polyols with high acid values by esterification of carboxylic acid functionality with primary polyols to produce highly useful ester polyols.

Branched primary polyols have been shown to be effective in inhibiting phase separation and precipitation. Therefore, the present invention seeks to incorporate branched primary polyols in the ester alcohol structure found in lubricants.

Specifically, in the present invention, the ester polyols and polyol esters have branched polyols that hinder close packing of the polyol ester chains, thus inhibiting crystallization. Further, the present invention shows that the amount of carboxylic acid groups used in esterification affects the viscosities, molecular weights, and crosslinking of the ester polyol and polyol ester. Lubricants, foams, and polyurethane coatings formed from esters polyols and polyol esters of the present invention have improved physical properties, such as, viscosity, pour point, and molecular weight.

In ester polyols, the presence of hydroxyl functionality and the selection of a hydroxyl/carboxyl ratio (HCR) is responsible for excess hydroxyl content or the hydroxyl value (HV) of the product polyol. This is achieved by the relative amounts of primary polyol and the amounts of carboxylic acid group containing compounds, both diacids and monoacids, in the polyol synthesis. Thus, the higher the amount of primary polyol, the higher the resulting hydroxyl value (HV) of the product polyol.

In one approach to produce ester polyols by esterification of ozone acids in the presence of excess primary polyols, the reproducibility and quality of the product ester polyol is sometimes difficult to control due to variations in reaction temperatures, gaseous sparge rates or applied vacuum. In another approach to prepare ester polyols by ozonolysis in solution, addition of excess ozone can lead to oxidation of primary polyol hydroxyl functionality to produce non-desired carboxylic acid functionality.

One aspect of the present invention is to provide a means to repair off-specification ester polyol to achieve product conforming to specified properties. This can be accomplished by analyzing the ester polyol and based on this analysis incorporating an additional primary polyol by a transesterification process to form the desired product polyol. Another aspect of the present invention is that currently, production of the three main types of ester polyols for polyurethane applications (flexible foam, rigid foam and coatings) by solvent-based ozonolysis methods requires ozone to be administered under three different sets of reaction conditions. The present invention allows the production of all three type ester polyols while only needing to prepare the type ester polyol having the lowest hydroxyl value by ozonolysis. Flexible foam polyols generally have the lowest hydroxyl value.

BRIEF DESCRIPTION OF THE FIGURES

The accompanying figures, which are incorporated in and constitute a part of this specification, illustrate aspects of the invention and, together with a general description of the invention given above, and the detailed description given below, serve to explain the invention.

DEFINITIONS

Figure 1:
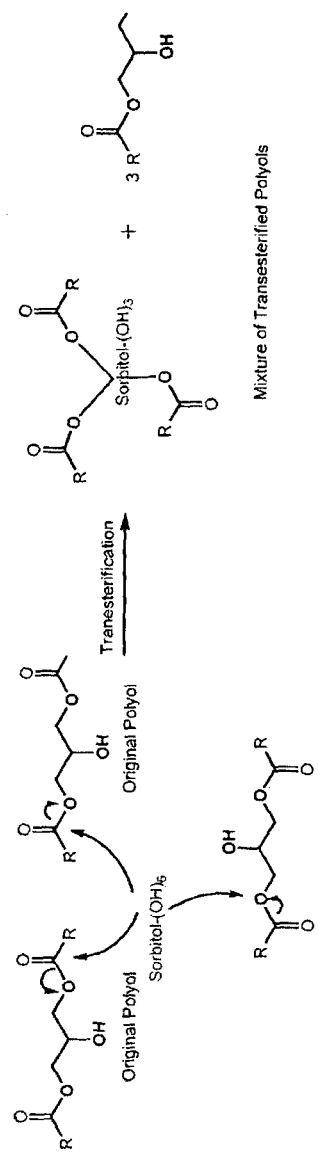
FIG. 1 illustrates the transesterification of a polyol with sorbitol.

For the purposes of the present invention, the method of the present invention may also be referred to as 'the master batch method' or the "master batch approach".

For the purposes of the present invention, the term 'comprising' refers to where various compounds, components, ingredients, or steps, can be conjointly employed in practicing the present invention. Accordingly, the term 'comprising' encompasses the more restrictive terms 'consisting essentially of', 'consisting of' and 'having'. With the term 'consisting essentially of' it is understood that the method of the present invention 'substantially' comprises the indicated compound, component, ingredient or step as 'essential' element.

For the purposes of the present invention, the term 'feedstock' is understood to mean any substance having at least one carbon-to-carbon double bond as defined herein the specification. The term feedstock also refers to any alkene or olefin comprising at least one carbon-to-carbon double bond.

For the purposes of the present invention, the phrase 'substance having at least one carbon-to-carbon double bond' may comprise any biobased or non-biobased substance, compound, and/or material having at least one carbon-to-carbon double bond. The term 'substance', 'compound,' and/or 'material' may be used interchangeably herein the present invention.

For the purposes of the present invention, the term 'biobased substance' used herein in the present invention may be understood to mean any substance, compound, and/or material that may be derived from any living matter and may comprise at least one carbon-to-carbon double bond. In particular, the biobased substance may comprise any lipids, waste biomass, biobased products, vegetable oil, animal fat, fatty acids, and/or fatty acid esters, and the like.

For the purposes of the present invention, the term 'fatty acid' is understood to mean any carboxylic acid (—COOH) with a long aliphatic chain, which may be saturated or unsaturated. For example, fatty acids may be derived from the hydrolysis of triglycerides or phospholipids. In particular, the fatty acid may be selected from the group consisting of: palm fatty acids, palm kernel fatty acid distillate, tallow fatty acids, fractionated tallow fatty acids, fractionated palm fatty acid distillate, and fractionated palm kernel fatty acid distillate and fatty acids of the soybean oil, safflower oil, linseed oil, corn oil, sunflower oil, olive oil, canola oil, sesame oil, cottonseed oil, mustard oil, camelina oil, jatropha oil, peanut oil, coconut oil, rapeseed oil, Chinese tallow oil, tung oil, castor oil, fish oil, algae oil, wheat germ oil, soya oil, hemp oil, or the like and a mixture thereof.

For the purposes of the present invention, 'fatty acid esters' may be, but are not limited to, obtained by transesterification of lipids or esterification of fatty acids obtained by hydrolysis of triglycerides, or any other methods known in the art.

The term 'lipids' used herein in the present invention is understood to mean any organic compounds comprising at least a chain of hydrocarbons, including, but are not limited to, vegetable oils, animal fats, fatty acids, fatty acid esters and the like. For example, lipids may comprise triglycerides.

Triglycerides are esters, which may be derived from a glycerol molecule and three molecules of fatty acids. Suitable examples of triglycerides include vegetable oil and animal fat. In particular, the triglyceride may be selected from soybean oil, safflower oil, linseed oil, corn oil, sunflower oil, olive oil, canola oil, sesame oil, cottonseed oil, mustard oil, camelina oil, jatropha oil, peanut oil, coconut oil, rapeseed oil, Chinese tallow oil, tung oil, castor oil, algae oil, wheat germ oil, soya oil, hemp oil, fish oil, tallow, duck fat, butter, or the like and a mixture thereof.

Lipids may also encompass glyceride molecules, such as, fatty acids and their derivatives, including fatty acid esters. Suitable examples of lipids include, but are not limited to, palm oil, palm oil fatty acids, olein, olein fatty acids, soybean oil, tallow, tallow fatty acids, safflower oil, linseed oil, corn oil, sunflower oil, olive oil, canola oil, sesame oil, cottonseed oil, mustard oil, camelina oil, jatropha oil, peanut oil, coconut oil, rapeseed oil, Chinese tallow oil, tung oil, castor oil, fish oil, algae oil, wheat germ oil, soya oil, and hemp oil.

Byproducts of the above-mentioned oils and lipids, such as palm fatty acid distillates (PFAD), palm kernel fatty acid distillates, fractionated palm fatty acid distillate, and fractionated palm kernel fatty acid distillate, fatty acids of soybean oil, palm fatty acid alkyl esters, alkyl esters of any biobased oils or fats, or the like, or a mixture, or a fraction thereof may also be used as the biobased substance. In a particular aspect of the present invention, the substance having at least one carbon-to-carbon double bond may comprise a lipid.

In particular, the substance having at least one carbon-to-carbon double bond may be a vegetable oil. More particularly, the substance having at least one carbon-to-carbon double bond may be palm oil or palm olein.

Further, the substance having at least one carbon-to-carbon double bond may comprise a fatty acid ester. In particular, the fatty acid ester may be a palm fatty acid alkyl ester.

Non-biobased substance used herein in the present invention may be understood to mean any substance comprising a compound, material and/or matter that are not derived from any living matter, and having at least one carbon-to-carbon double bond. In particular, the non-biobased substance may be synthesized from hydrocarbon, petrochemical, fossil fuel, crude oil, and the like. Even more in particular, the non-biobased substance may comprise at least one alkene.

An azeotrope composition is understood to mean a composition of two or more components characterized by a constant minimum or maximum boiling point which is respectively lower or higher than that of either component, and wherein the azeotrope distillate at this boiling point is a constant composition that is not related to the relative concentrations of the two or more components. For example, the azeotropic distillate composition of ethanol/water is close to a ratio of 96/4 and that of 1-butanol/water is close to a ratio of 57.5/42.5, regardless of their respective solution compositions, as long as both water and alcohol components remain in the distillation vessel. Accordingly, to 'azeotrope with water' is understood to mean 'to form an azeotrope composition with water'. For example, a solvent that azeotropes with water is understood to mean any solvent that forms an azeotrope composition when mixed with water.

More particularly, the water content of an azeotrope of ethanol with water is about 4.0%. The water content of the azeotropic composition of 1-butanol and water is about 42.5%. The water content of the azeotropic composition of 1-hexanol and water is about 33.0%. The water content of the azeotropic composition of 1-octanol and water (boiling point: 195.0° C.) is about 90.0%.

'Monoalcohol' is understood to mean any monohydric alcohol, i.e., an alcohol having only one hydroxyl group. 'Polyol' is understood to mean any polyhydric alcohol, i.e., an alcohol having more than one hydroxyl group.

An ester polyol according to the invention comprises the structure:

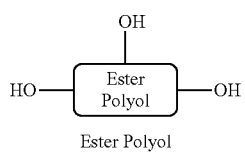

Ester Polyol

Ester polyols prepared by the method of the invention may be referred to as 'product polyols'. For example, ester polyols may comprise Azelaic di(monoglyceride), Nonanoic monoglyceride, Malonic di(monoglyceride), Hexanoic monoglyceride, Propanoic monoglyceride, Palmitic monoglyceride, and Stearic monoglyceride.

An ester polyol ester according to any aspect of the invention comprises the structure:

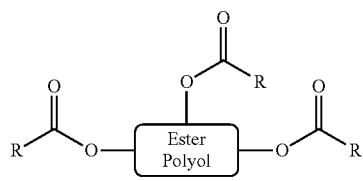

For the purposes of the invention, the terms 'cleaved alkyl esters' and 'ozone esters' are used interchangeably to refer to esters formed by ozonolysis of a substance having a carbon-to-carbon double bond in the presence of an alcohol to form cleaved alkyl esters, which may be intermediates in producing the final polyol ester product. Similarly, the term 'ozone acid' may be used to refer to carboxylic acids formed by ozonolysis of a substance having a carbon-to-carbon double bond. For example, ozonolysis of fatty acids cleaves the double bond of the fatty acids and produces a mixture of ozone acids, which may comprise for example azelaic, pelargonic (nonanoic), malonic, hexanoic, and propionic acids.

For the purposes of the invention, 'resin-bound acid catalyst' is understood to mean any acid catalyst which has been immobilized on a resin substrate, for example SiliaBond® propylsulfonic acid, or Amberlite® IR-120 (macroreticular or gellular resins or silica covalently bonded to sulfonic acid or carboxylic acid groups). One advantage of a solid acid or resin-bound acid catalyst is that it can be removed from the reaction mixture by simple filtration.

The terms 'reflux' and 'refluxing' are used interchangeably and are understood herein in the present invention to mean to boil the reaction mixture in a vessel attached to a condenser such that the vapors continuously condense for reboiling. The term 'reflux temperature' is then understood to mean the temperature at which refluxing occurs.

In particular, a step of refluxing, before the addition of a second mole of ozone may further comprise any means, apparatus, methods, and/or techniques to separate water from the condensed distillate obtained by azeotropic distillation. Azeotropic distillation in the present invention may include separating an azeotrope composition by distillation. For example, an azeotropic distillation may include the technique of adding another component to generate a new, lower-boiling azeotrope that is heterogeneous (i.e., producing two, immiscible liquid phases, such as, water and the condensed distillate). This may include, but is not limited to, the use of a Barrett or Dean-Stark apparatus to separate water from the condensed distillate obtained by azeotropic distillation.

For the purposes of this invention, 'virtual ozone acids' or 'simulated ozone acids' are compositions of acids expected to be produced from exemplary feedstock, for example fractionated oleic acid nominally containing 72 percent oleic acid may be 'simulated' using Edenor OL-72 produced by Emery Oleochemicals.

DETAILED DESCRIPTION OF THE INVENTION

The present inventors have addressed the problems in the art and have developed the master batch method, an improved method for preparing ester polyols suitable for a range of applications.

Accordingly, in one aspect the present invention is provided a method for preparing ester polyols comprising transesterifying a first ester polyol with a primary polyol to produce a second ester polyol, the second ester polyol having a hydroxyl value (HV) which is greater than a hydroxyl value ($HV_i$) of the first ester polyol.

In one particular aspect of the invention, the first ester polyol may be prepared by the sequential steps of:
reacting a fatty acid distillate with ozone in the presence of a reactant and a catalyst to produce a reaction mixture, wherein the ozone may comprise at least two moles of ozone per carbon-to-carbon double bond of the fatty acid distillate; and
refluxing the reaction mixture to produce the first ester polyol having a hydroxyl value ($HV_i$). The fatty acid distillate may be a palm fatty acid distillate. The hydroxyl value of the second ester polyol may be greater than about 300.

In one particular aspect of the invention, the reactant may be a solvent. In particular, the solvent may be selected from ethyl acetate, methyl acetate, ethyl propionate, methyl propionate, ethyl butyrate, methyl butyrate, ethyl isobutyrate, butyl acetate, butyl butyrate, isobutyl isobutyrate, or a mixture thereof.

In one particular aspect of the invention, the catalyst may be an acid catalyst. In particular, the acid catalyst may be a resin-bound acid catalyst. More in particular, the acid catalyst may be selected from Sulfuric acid (H2SO4), resin-bound propanesulfonic acid, and propanesulfonic acid.

In one particular aspect of the invention, the first ester polyol may be prepared by the sequential steps of:
hydrolyzing a triglyceride to produce at a mixture of fatty acids;
esterifying the mixture of fatty acids with at least one monoalcohol to form at least one fatty acid alkyl ester;
performing fractionation by distillation of the at least one fatty alkyl acid ester to partially remove saturates;
reacting the at least one fractionated fatty alkyl acid ester with ozone to produce a mixture of ozone esters, wherein the ozone comprises one mole of ozone per carbon-to-carbon double bond of the at least one fractionated fatty alkyl acid ester; and
transesterifying the mixture of ozone esters with a primary polyol to produce the first ester polyol having a hydroxyl value ($HV_i$). The hydroxyl value of the second ester polyol may be greater than about 316. The second ester polyol may have an acid value (AV) of less than about 0.9.

In one particular aspect of the invention, the at least one monoalcohol may comprise 1-butanol or isomers thereof, 1-pentanol or isomers thereof, 1-hexanol or isomers thereof, 1-heptanol or isomers thereof, 1-octanol or isomers thereof, 1-nonanol or isomers thereof, 1-decanol or isomers thereof, 1-undecanol or isomers thereof, 1-dodecanol or isomers thereof, 1-tridecanol or isomers, 1-tetradecanol or isomers thereof, cetyl alcohol or isomers, or stearyl alcohol or isomers thereof. In particular, the at least one alcohol may be methanol. Alternatively, the at least one alcohol may be 1-butanol. Alternatively, the at least one alcohol may be 1-hexanol.

In one particular aspect of the invention, the saturates may comprise palmitic and/or stearic esters.

In one particular aspect of the invention, the transesterifying the mixture of ozone esters and the first ester polyol may be in the presence of a tin catalyst. In particular, the tin catalyst may be selected from a tin oxalate or tin oxide catalyst In one particular aspect of the invention, the triglyceride may be selected from palm oil, olein, palm fatty acid distillate (PFAD) or palm kernel fatty acid distillate (PKFAD).

In one particular aspect of the invention, the first ester polyol may be prepared by the sequential steps of:
reacting a substance having at least one carbon-to-carbon double bond with ozone in the presence of at least one monoalcohol that azeotropes with water and at least one solvent to produce a plurality of ozone esters, wherein the ozone comprises at least one first mole of ozone and at least one second mole of ozone and wherein the reacting step comprises refluxing the substance having the at least one carbon-to-carbon double bond before adding the second mole of ozone; and
transesterifying the plurality of ozone esters with a primary polyol to produce the first ester polyol having a hydroxyl value ($HV_i$).

In one particular aspect of the invention, the at least one solvent may comprise at least one solvent that azeotropes with water. In particular, the at least one solvent that azeotropes with water may be selected from ethyl acetate, methyl acetate, ethyl propionate, methyl propionate, ethyl butyrate, methyl butyrate, ethyl isobutyrate, butyl acetate, butyl butyrate, isobutyl isobutyrate, or a mixture thereof. More in particular, the at least one solvent that azeotropes with water may be butyl acetate. Alternatively, the at least one solvent that azeotropes with water may be ethyl isobutyrate.

In one particular aspect of the invention, the reacting step may further comprise an acid catalyst. In particular, the catalyst may be an acid catalyst. More in particular, the acid catalyst may be a resin-bound acid catalyst. Yet further in particular, the acid catalyst may be selected from Sulfuric acid (H2SO4), resin-bound propanesulfonic acid, and propanesulfonic acid.

In one particular aspect of the invention, the at least one monoalcohol that azeotropes with water may comprise at least one monoalcohol with at least four carbon atoms. In particular, the at least one monoalcohol that azeotropes with water may comprise 1-butanol or isomers thereof, 1-pentanol or isomers thereof, 1-hexanol or isomers thereof, 1-heptanol or isomers thereof, 1-octanol or isomers thereof, 1-nonanol or isomers thereof, 1-decanol or isomers thereof, 1-undecanol or isomers thereof, 1-dodecanol or isomers thereof, 1-tridecanol or isomers thereof, 1-tetradecanol or isomers thereof, cetyl alcohol or isomers thereof, or stearyl alcohol or isomers thereof. In particular, the at least one monoalcohol that azeotropes with water may comprise a water-soluble lower alcohol. More in particular, the at least one monoalcohol that azeotropes with water may comprise 1-butanol. Alternatively, the at least one monoalcohol that azeotropes with water may comprise 1-hexanol.

In one particular aspect of the invention, the at least one monoalcohol that azeotropes with water may form an azeotrope composition, and the azeotrope composition may have a water content from a range of 4 to 90 percent water. In particular, the azeotrope composition may have a water content from a range of 20 to 60 percent water. More in particular, the azeotrope composition may have a water content from a range of 30 to 50 percent water.

In one particular aspect of the invention, the reacting step may comprise reacting the substance having at least one carbon-to-carbon double bond in the presence of an ozonolysis catalyst. In particular, the ozonolysis catalyst may be selected from a Lewis acid and Bronsted acid.

In one particular aspect of the invention, the substance having at least one carbon-to-carbon double bond may comprise a vegetable oil and/or animal fat. In particular, the vegetable oil may be selected from soybean, safflower, linseed, corn, sunflower, olive, canola, sesame, cottonseed, mustard, camelina, jatropha, peanut, coconut, rapeseed, Chinese tallow, tung, castor, algae, wheat germ, soya, hemp, and palm oil. More in particular, the vegetable oil may comprise palm oil. Alternatively, the animal fat may be selected from fish oil, lard, duck fat, butter, and a mixture thereof.

In one particular aspect of the invention, the substance having at least one carbon-to-carbon double bond may comprise a fatty acid. In particular, the fatty acid may be selected from the group consisting of: palm fatty acid distillates, palm kernel fatty acid distillates, fractionated palm fatty acid distillate, olein fatty acids, fractionated olein fatty acids, tallow fatty acids, fractionated tallow fatty acids, fractionated palm kernel fatty acid distillate, and fatty acids of the soybean oil, safflower oil, linseed oil, corn oil, sunflower oil, olive oil, canola oil, sesame oil, cottonseed oil, mustard oil, camelina oil, jatropha oil, nuts oil, peanut oil, coconut oil, rapeseed oil, Chinese tallow oil, tung oil, castor oil, wheat germ oil, soya oil, hemp oil, fish oil, algae oil, and the like and a mixture thereof.

In one particular aspect of the invention, the substance having at least one carbon-to-carbon double bond may comprise a fatty acid ester. In particular, the fatty acid ester may comprise a palm fatty acid alkyl ester.

According to any aspect of the invention, the primary polyol may be selected from glycerin, trimethylolpropane, pentaerythritol, 1,2-propylene glycol, 1,3-propylene glycol, 2-methyl-1,3-propanediol, 1,4-butanediol, ethylene glycol, glucitol fructose, glucose, sucrose, aldoses, ketoses, alditols, disaccharides, or combinations thereof The transesterification of a starting ester polyol with one or more primary polyols can be used to prepare a modified ester polyol having different crosslinking properties and hydroxyl value (HV). By adjusting the reaction conditions, the HV of the final product can be controlled. This transesterification typically occurs under non-release conditions where no byproducts are allowed to escape.

A schematic of this process is shown in FIG. 1 where a starting ester polyol is being transesterified with the primary polyol sorbitol. The stoichiometry will depend on the combining ratios. In FIG. 1, three of sorbitol's six hydroxyl groups are involved in transesterification reactions with a starting ester polyol that has diglyceride functionality. The portions of the original polyol that become covalently attached to sorbitol now have an increased degree of crosslinking. The final number of hydroxyl groups is the sum of the hydroxyl groups in the starting materials (9 hydroxyl groups) so that the hydroxyl value (HV) of the final polyol mixture will have increased over its original value. Thus, the Master Batch approach for any ester polyol preparation method involves making the lowest HV polyol (typically a flexible foam polyol) and then separately converting this polyol to a coating or rigid foam ester polyol by adding the appropriate amount and type of polyols needed to provide the final polyol hydroxyl value (HV) and degree of crosslinking. As shown in FIG. 1, the product polyol can also have increased crosslinking as well as increased hydroxyl value (HV).

Figure 2:
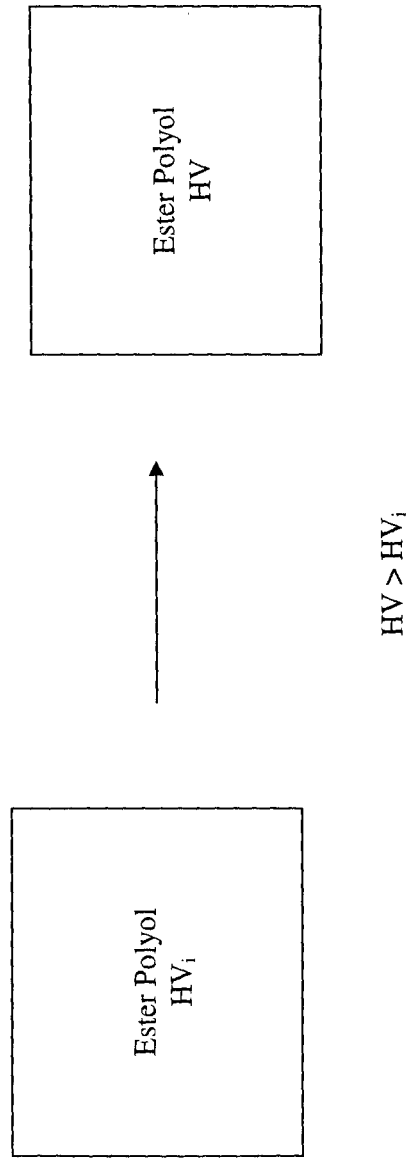
FIG. 2 shows a simplified block diagram of a process of the present invention.

FIG. 2 shows a simplified block diagram of a process of the present invention. An ester polyol is transesterified to produce an ester polyol where the hydroxyl value ($HV_i$) of the initial ester polyol is less than the hydroxyl value (HV) of the product polyol.

The procedure for the preparation of the modified ester polyols is based on the transesterification reaction of an ester polyol with a primary polyol. Three different methods have been developed for preparing ester polyols and data is presented to show that the master batch process is applicable to ester polyols produced by each method. After the ester polyol is formed by one of these methods, the ester polyol is transesterified to produce an ester polyol having a higher hydroxyl value ($HV_2$) than the original hydroxyl value ($HV_1$) of the initial ester polyol (where $HV_2 > HV_1$).

Three methods are used in preparing ester polyols, referred to as methods 1, 2 and 3. Method 1 is a solvent-based approach that produces an ester polyol by reacting a fatty acid-based triglyceride with ozone in the presence of a primary polyols and ozonolysis catalyst and refluxing the reaction mixture (WO2007/027223). Method 2 produces intermediate ozone acids by the oxidative ozonolysis of fatty acids and the ozone acids are esterified with primary polyols to produce ester polyols (WO2010/078505). Method 3 involves the ozonolysis of fatty acid-based triglycerides, fatty acid esters or fatty acids in solution in the presence of monoalcohols and an ozonolysis catalyst to form intermediate cleaved alkyl esters that are then transesterified with primary polyols to form ester polyols.

One of the differences between the first and third method is that the third method includes a reaction in the presence of a monoalcohol that azeotropes with water and a solvent to produce the ozone esters. The third method of producing an ester polyol uses a reduced amount of ozone compared to the first ozonolysis method.

The Master Batch approach involves the preparation of an ester polyol having a low hydroxyl value (HV), for example a flexible foam ester polyol, and then transesterifying with specific components needed to increase the product ester polyol HV and/or providing crosslinking as needed. This approach allows the preparation of a flexible foam ester polyol which may be converted to coating and rigid foam ester polyols.

The Master Batch Approach Applied to Method 1

The Master Batch approach using Method 1 can use unmodified palm oil as the starting material or feedstock to produce the initial ester polyol. The ozonolysis reaction of the feedstock is in the presence of a solvent and a catalyst. The solvent is selected from ethyl acetate, methyl acetate, ethyl propionate, methyl propionate, ethyl butyrate, methyl butyrate, ethyl isobutyrate, butyl acetate, butyl butyrate, isobutyl isobutyrate, or a mixture thereof.

Primary polyols, such as, trimethylolpropane (TMP) or glycerin that are preferred for lubricant applications are vulnerable to oxidation in the presence of ozone leading to acid structures that raise the product acid value, which is not desirable for lubricant applications. Glycerin and TMP also require pre-esterification to raise the hydroxyl value (HV) of ester polyols due to low solvent solubilities. Further, many primary polyols have limited solubility in acceptable solvents that necessitates a pre-esterification step at an additional cost, especially higher boiling ester solvents, such as ethyl isobutyrate.

Figure 3:
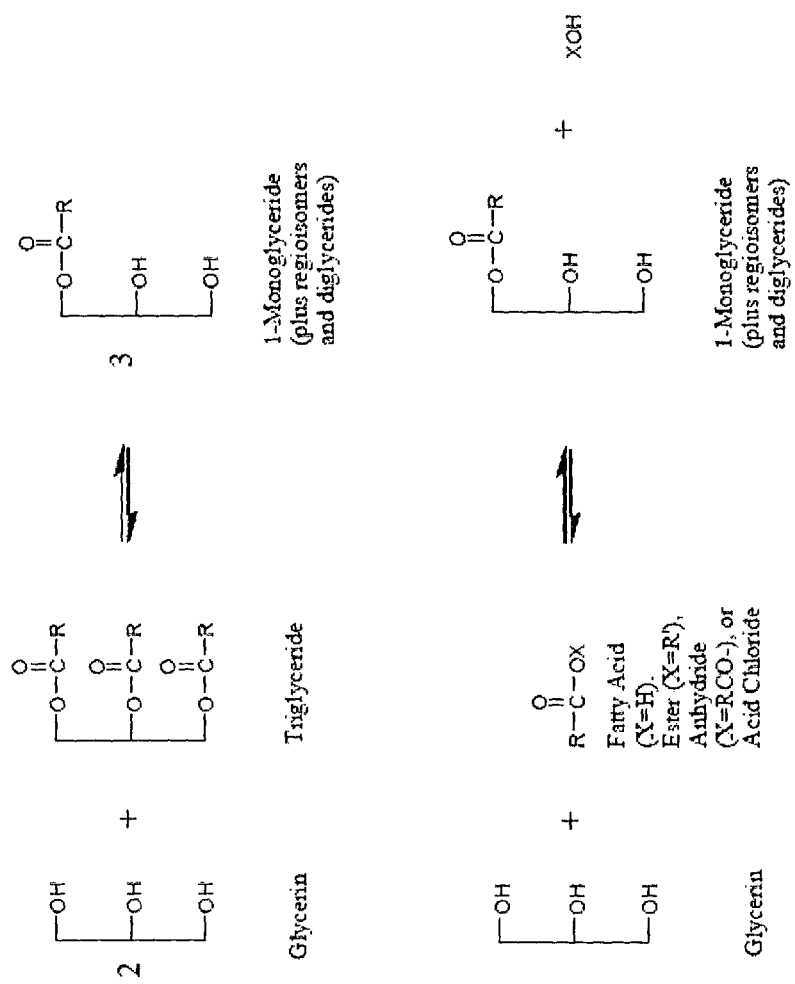
FIG. 3 illustrates the pre-esterification of glycerin.

FIG. 3 illustrates the pre-esterification of glycerin, which enhances solubility in various solvents. As shown in FIG. 3, primary polyol pre-esterification can be performed by reacting the primary polyol with an appropriate triglyceride, fatty acid, fatty acid ester, anhydride, or acid chloride. Use of pre-esterified primary polyols in ester solvents also appreciably increases the solubility of glycerin due to the presence of the solubilized hydroxylated components.

The use of a modified oil, which has been transesterified to esters at the fatty acid glyceride sites before reacting with the ozone and excess alcohol, as shown in FIG. 3, allows the production of hybrid $C_9$ or azelate esters (the major component in the reaction mixture) where the ester on one end of the azelate diester is different from the ester on the other end. In order to produce a hybrid ester composition, the alcohol used in ozonolysis is different from the alcohol used to transesterify the esters at the fatty acid glyceride sites.

Figure 4:
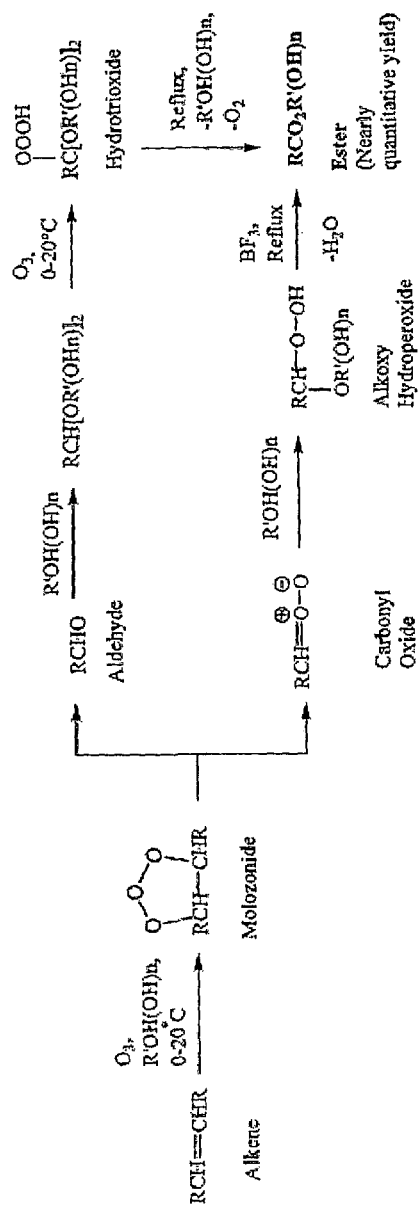
FIG. 4 is a schematic depicting the steps involved in converting a substance having a carbon-to-carbon double bond by ozonolysis in the presence of an alcohol to cleaved alkyl esters as intermediates to produce the final polyol ester product.

FIG. 4 shows Method 1 of producing an ester polyol. Method 1 is a low temperature ozonolysis of fatty acids that produces an ester alcohol product. If a primary polyol, such as, glycerin is used in this process (and in excess) that mainly one hydroxyl group will be used to generate ester functionality and the remaining alcohol groups will remain pendant in generating ester glycerides. One method involves the combined ozonolysis and transesterification of a biobased oil, oil derivative, or modified oil to produce esters. As shown in FIG. 4, if the feedstock is a substance having a carbon-to-carbon double bond where the substituent R is an alcohol, an ester polyol is made.

In FIG. 4, ozonolysis of a substance having a carbon-to-carbon double bond or alkene was performed in the presence of a catalyst at about 0-20° C. in an alcohol as the reactive solvent. Method 1 typically includes the use of an ozonolysis catalyst. The ozonolysis catalyst is generally a Lewis acid or a Bronsted acid. Suitable catalysts include, but are not limited to, boron trifluoride, boron trichloride, boron tribromide, tin halides (i.e., tin chlorides), aluminum halides (i.e., aluminum chlorides), zeolites (solid acid), molecular sieves (solid acid), sulfuric acid, phosphoric acid, boric acid, acetic acid, and hydrohalic acids (i.e., hydrochloric acid). The ozonolysis catalyst can be a resin-bound acid catalyst, such as, SiliaBond propylsulfonic acid, or Amberlite® IR-120 (macroreticular or gellular resins or silica covalently bonded to sulfonic acid or carboxylic acid groups). One advantage of a solid acid or resin-bound acid catalyst is that it can be removed from the reaction mixture by simple filtration.

Method 1 can generally take place at a temperature in a range of about −80° C. to about 80° C., preferably about 0° C. to about 40° C., more preferably about 10° C. to about 20° C. The process can take place in the presence of a solvent, if desired. Suitable solvents include, but are not limited to, ester solvents, ketone solvents, chlorinated solvents, amide solvents, or combinations thereof. Examples of suitable solvents include, but are not limited to, ethyl acetate, acetone, methyl ethyl ketone, chloroform, methylene chloride, and N-methylpyrrolidinone.

The reaction mixture was then refluxed typically one hour in the same reaction vessel. Ozone was then restarted and sparged into the mixture for 13 hours longer at 45° C. The mixture was then refluxed 2 hours longer.

The solution was then dried with magnesium sulfate and filtered. The product was purified by short path distillation to obtain a clear and light yellow liquid. When the alcohol is a polyol, an ester polyol is produced. Suitable polyols include, but are not limited to, glycerin, trimethylolpropane, pentaerythritol, or propylene glycol, alditols, such as, sorbitol and other aldoses and ketoses, such as, glucose and fructose.

As shown in FIG. 4, Method 1 uses two moles of ozone for each double bond, which increases the cost of the production. In addition, the second mole of ozone reacts much more slowly than the first requiring a two-Stage reactor and making the primary polyol oxidation more likely. Method 1 ester polyols typically have high acid values (AV) that require mitigation by tin-catalyzed self-esterification.

When primary polyols that are susceptible to oxidation are used in Method 1, the resulting products may be impaired by having high carboxylic acid content. For example, at low hydroxyl to reactive site ratios, polyacids may form in addition to ester polyols. To mitigate the undesirable oxidation of the primary polyol, it is advantageous to use the lowest possible ratio of primary polyol to reactive group. However, impaired material or polyacid may be converted via Method 1 into flexible and rigid foam polyols that met desired structural specifications and also produced high performance foam products. This is an example of one aspect of the Master Batch approach where a starting polyol with a low $HV_i$ or even a polyacid can be converted as desired by transesterification of additional primary polyol, to obtain higher HV materials suitable for a variety of uses.

The use of a solvent in the presence of a powerful oxidant, such as, ozone will require additional safety controls. The use of a solvent requires efficient capture and recycling or higher costs will result. Incomplete conversion of intermediate acetals will lead to product polyols that are subject to oxidative and hydrolytic instability, which is not recommended for many lubricant applications. Presently, Method 1 produces ester polyols with a limited range of polyol molecular weights. The acid neutralization process using a basic water wash can solubilize low molecular weight polyol resulting in greatly decreased yields complicating isolation and raising product costs.

In Table A, the starting material was LRB 52781-107-5 ("107") that has a 1.10 hydroxyl/reactive site ratio.

The starting material (52781-107-5) was characterized by a hydroxyl value (HV) of 14.4 and an acid value (AV) of 27.6. For reference, the flexible foam polyol starting material was referred to as a polyacid 107.

The target products after esterification and transesterification of polyacid 107 were a rigid foam polyol with a hydroxyl value (HV) of 354 and flexible foam polyol with a hydroxyl value (HV) of 61, which correspond to the rigid foam polyol 17 and flexible foam polyol 18 of Method 2. The products formed using Method 1 after esterification and transesterification of polyacid 107 were a rigid foam polyol with a hydroxyl value (HV) of 300 and flexible foam polyol with a hydroxyl value (HV) of 15.8. Both of the resulting hydroxyl value (HV) values were approximately 40-50 HV units lower than expected. This is attributed to the fact that the glycerin used for both transesterifications retained moisture in Method 1. Another drawback of glycerin is that glycerin underwent extensive oxidation when a low molecular weight polyol was targeted.

These results are summarized in Table A.

TABLE A

Method 1 Rigid and Flexible Foam Polyols Obtained from Polyacid 52781-107-5
Rigid and Flexible Foam Ester Polyols obtained by applying the Master Batch Approach to Method 1 Ester Polyols

|     | Starting Material | Rigid Foam Target | Polyol Obtained Polyol | Flexible Foam Target | Polyol Obtained Polyol |
| --- | --- | --- | --- | --- | --- |
| LRB | 52781-107-5 "Polyacid 107" | 52781-17-33 | 52921-5-22 | 52781-18-31 | 52921-4-24 |
| HV  | 14.4 | 354 | 300 | 61 | 15.8 |
| AV  | 27.6 | 0.9 | 0.0 | 0.8 | 0.0 |

The Master Batch Approach Applied to Method 2

Method 2 involves the initial production of ozone acids from fatty acids to produce ozone acids and subsequent esterification of these ozone acids with a polyol or mixture of polyols to produce ester polyols. Our evaluation of Method 2 started with the esterification of virtual ozone acids having a composition similar to the ozone acids expected from ozonolysis of exemplary palm feedstocks. Virtual ozone acid mixtures were readily esterified with mixtures of primary polyols in high yields.

In particular, virtual ozone acids were simulated for the ozonolysis of fractionated PFAD and palm fatty acids, which are examples of appropriate starting materials for Method 2. Virtual ozone acids corresponding to fractionated PFAD feedstock were esterified with either a single primary polyol or mixtures of primary polyols using tin oxide as the esterification catalyst. The hydroxyl/carboxyl ratios were varied from a high value of 2.48 to a low value of 1.10. The ester polyols prepared from these feedstocks typically had viscosities, crystallization onset temperatures (COTs), and percent volatilization at 250° C. that were too high for hydraulic oil applications. However, capping of specific ester polyols obtained from fractionated PFAD using different capping acids was found to advantageously result in reduced viscosities, COTs, and volatilization values that matched those required for high volume hydraulic oils. Thus, a range of ester polyols were prepared that fit the requirements for hydraulic oil base materials, as well as, polyurethane-derived rigid and flexible foams and coatings.

Further, in esterifying virtual ozone acids expected from ozonlysis of full composition PFAD, A series of ester polyols were prepared using the primary polyols glycerin, TMP and Me-PG while varying the hydroxyl/carboxyl ratios from 1.85 to 1.10. It was found that partial replacement of glycerin with TMP would provide ester polyols with enhanced properties, in particular reduced phase separation as compared to ester polyols prepared without partial replacement of glycerin with TMP.

Figure 5:
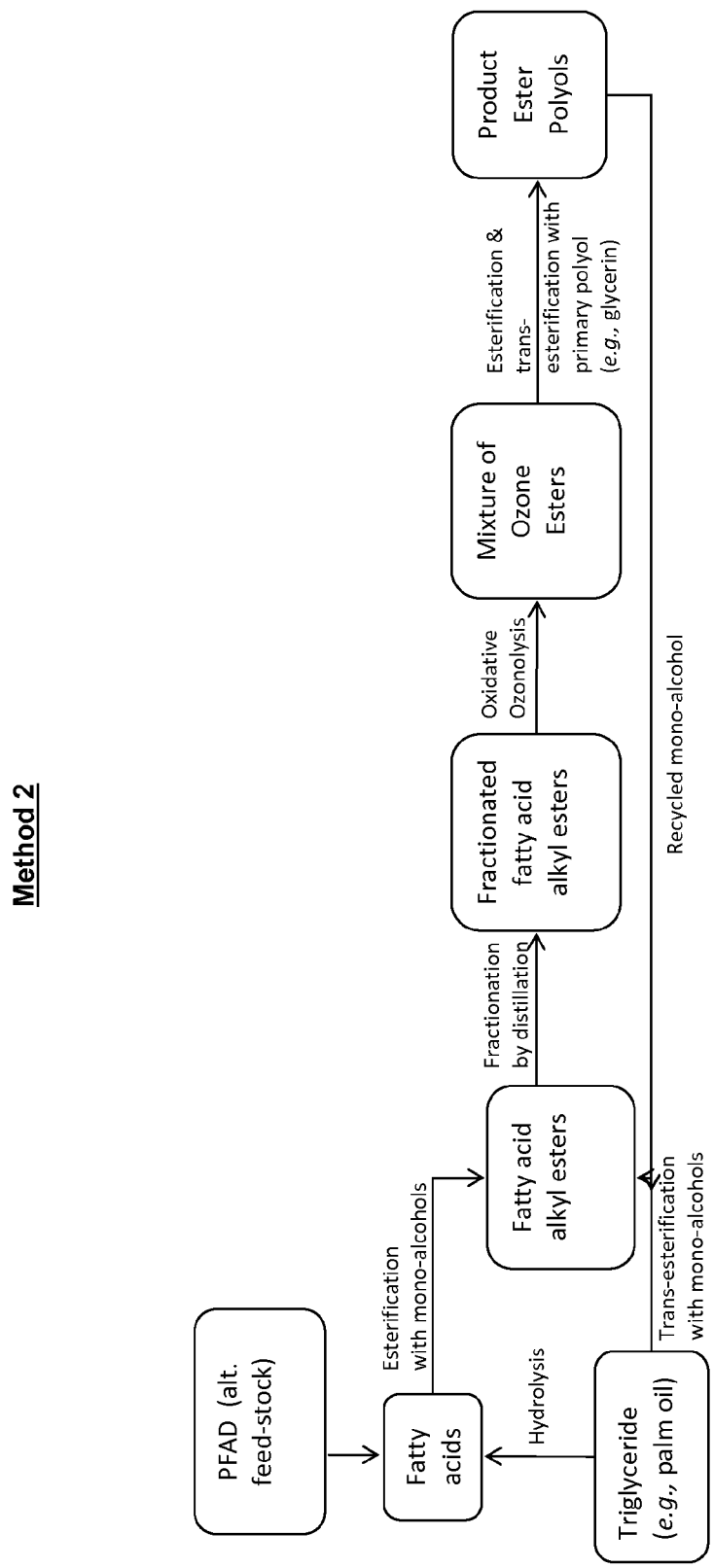
FIG. 5 is a flowchart illustrating the process of producing product ester polyols from triglycerides (e.g., palm oil) and/or palm fatty acid distillates (PFAD) via the step of ozonolysis of fatty acids in the presence of a monoalcohol that azeotropes with water into a mixture of cleaved alkyl esters (or ozone esters), preceded by the optional step of fractionation by distillation of the fatty acid alkyl esters, and transesterification in the presence of a primary polyol (e.g., glycerin).

FIG. 5 is a simplified block diagram depicting the process steps according to Method 2 to produce an ester polyol via oxidative ozonolysis of fractionated fatty acid alkyl esters. Feedstock such as palm oil, olein, or palm fatty acid distillates (PFAD) when subjected to hydrolysis provide a source of fatty acids. Generally, the feedstock may be hydrolyzed by steam splitting to generate fatty acids. The fatty acids are then esterified with a monoalcohol that azeotropes with water to produce fatty acid alkyl esters. The monoalcohol that azeotropes with water may be used with or without another azeotropic solvent. The monoalcohol can be selected from methanol, 1-butanol or isomers thereof, 1-pentanol or isomers thereof, 1-hexanol or isomers thereof, 1-heptanol or isomers thereof, 1-octanol or isomers thereof, 1-nonanol or isomers thereof, 1-decanol or isomers thereof, 1-undecanol or isomers thereof, 1-dodecanol or isomers thereof, 1-tridecanol or isomers, 1-tetradecanol or isomers thereof, cetyl alcohol or isomers, or stearyl alcohol or isomers. Alternatively, the fatty acid alkyl esters can be produced from the trans-esterification reaction between triglycerides and a monoalcohol.

The fatty acid alkyl esters are then fractionated by distillation where saturated esters, such as, palmitic and stearic esters are removed or partially removed from the mixture. After this, the fractionated fatty acid alkyl esters are subjected to oxidative ozonolysis where all available double bonds (unsaturated acids) will be broken down to produce mixtures of ozone esters containing mixtures of mostly saturated fatty acid alkyl esters. The oxidative ozonolysis may occur at near ambient temperatures using nonanoic acid as the reaction solvent to produce intermediate ozonides. The ozonides may be pumped into a secondary oxidizer unit operating at approximately 100-110° C. where oxygen will be passed through to generate a mixture of ozone esters. Specifically, the mixture of ozone esters may include an Azelaic hemiester; $C_3$, $C_6$, and $C_9$ monoacids; and palmitic and stearic alkyl esters.

Subsequently, the mixture of ozone esters is trans-esterified with primary polyols to form ester polyols. The primary polyol may be selected from glycerin, trimethylolpropane, pentaerythritol, 1,2-propylene glycol, 1,3-propylene glycol, 2-methyl-1,3-propanediol, 1,4-butanediol, ethylene glycol, glucitol fructose, glucose, sucrose, aldoses, ketoses, alditols, disaccharides, or combinations thereof. The use of a mixture of ozone esters provides property advantages and also eliminates the need to fractionate the various ozone esters from each other prior to trans-esterification. However, if a decreased saturated acid (e.g., palmitic and stearic acid) content is desired in the ozone esters, the mixture of ozone esters may be fractionated after oxidative ozonolysis.

As listed in Table B, the Master Batch approach was used in converting the flexible foam polyol (52781-94-33) produced by Method 2 to a rigid foam polyol (52781-101-28). The rigid foam polyol 101 obtained by this approach had a hydroxyl value (HV) that was 40-50 units lower than expected. This condition is also attributed to the use of glycerin as the primary polyol, which retained moisture.

TABLE B

Method 2 Rigid and Coating Polyols Obtained from Flexible Foam Polyol 5278 1-94-33 Rigid Foam Ester Polyols obtained by applying the Master Batch Approach to Method 2 Ester Polyols

| | | Rigid Foam Polyol | |
|---|---|---|---|
| | Starting Material | Target | Obtained Polyol |
| LRB | 52781-94-33 | 52781-17-33 | 52781-101-28 |
| HV | 56.2 | 354 | 316 |
| AV | 0.0 | 0.9 | [[ ]] |

As shown in Table B, the Master Batch approach was used in converting a Method 2 flexible foam polyol (52781-94-33) to a rigid foam polyol (52781-101-28). The rigid foam so obtained, polyol 101, had characteristics comparable to those of the foam obtained from a target polyol 17 (52781-17-33). In particular, the HV was raised from 56.2 to 316. Thus, the Master Batch approach can also be successfully applied to the Method 2 process. The esterification yields in the Method 2 were found to be essentially quantitative to the predicted values. Fractionated PFAD and palm fatty acids are appropriate starting materials for Method 2. Non-fractionated PFAD and palm fatty acids cannot be used due to ozonide viscosity restrictions. A range of ester polyols were prepared that fit the requirements for hydraulic oil base materials, as well as, polyurethane-derived rigid and flexible foams and coatings. Partial replacement of glycerin with TMP was found to provide ester polyols with enhanced phase maintaining properties that is important in full PFAD composition polyols.

Candidate polyols typically had viscosities, crystallization onset temperatures (COTs), and percent volatilization at 250° C. that are too high for hydraulic oil applications. Carboxylic acid capping evaluation studies were performed with up to five carboxylic acids on lubricant base polyols derived from both fractionated and non-fractionated PFAD. Capping of specific polyols obtained from fractionated PFAD was found to advantageously result in reduced viscosities, COTs, and volatilization values that matched those required for high volume hydraulic oils. An acid capping study of one polyol obtained from full composition PFAD (Polyol 11R) showed some reduction in these properties. However, the obtained polyol did not optimize the characteristics for use in hydraulic oil applications.

Based on the evaluation of these three performance properties, the best capping acid was nonanoic acid. Nonanoic acid will also significantly increase the percent biobased content of the derived hydraulic oils.

In this example of the present invention, a rigid foam polyol obtained by the Master Batch process provided a rigid foam whose performance was comparable to that obtained from the target rigid foam ester polyol Method 2 uses a minimal amount of high boiling solvent during the ozonolysis step, thus minimizing flammability concerns and costs. No solvent is used during the esterification step, which eliminates the need for recycling, thus decreasing costs. The Method 2 uses only one mole of ozone is used per double bond. The primary polyol is not exposed to ozone, thus eliminating competitive oxidation reactions. A wide range of polyol molecular weights and HV values have been demonstrated for applications in lubricants, foams, and coatings. Further, this method does not produce acetal intermediates so oxidative and hydrolytic stability is improved over Method 1 polyols, which is a key advantage for lubricant applications. The esterification catalysts are solids and can be removed by filtration in Method 2.

A drawback to applying the Method 2 polyol esters to the Master Batch approach is that the oxidative ozonolysis step requires a relatively low viscosity liquid feed. Therefore, unfractionated palm acids (PFAD) may not be eligible as a feedstock. Also, PFAD contains a significant fraction of mono- and di-glycerides, which may not be compatible with the oxidative ozonolysis process. Further, the oxidative ozonolysis step is conducted under conditions that will decarboxylate malonic acid resulting in approximately 2.5% mass loss.

The Master Batch Approach Applied to Polyols of Method 3

Method 3 is able to use a wide variety of feedstock, such as full composition or fractionated PFAD, PKFAD, palm oil and their derivatives due to their excellent solubility of the palm feedstock, 1-butanol, and butyl esters in the process solvents of Method 3. The variety of feedstock options provides the option of using a lower cost feedstock when the price of feedstock is volatile. Further, PKFAD polyols function as good lubricant candidates. Primary polyols are not present during the ozonolysis step, therefore there are no undesirable competitive oxidations.

Sulfuric acid is the preferred ozonolysis catalyst, which is cheaper than other catalyst acids. A solid ion-exchange resin (Amberlyte IRA-67) is used to neutralize the acid catalyst, thus washing is not required, resulting in nearly quantitative yields of product ester polyols. Solid tin catalysts are used for the transesterification step that can be easily removed by filtration. The tin catalysts may include a tin oxalate or tin oxide catalyst. A wide range of product polyols have been demonstrated with properties essentially equivalent to those from Method 2.

Two moles of ozone are required per mole of carbon-to-carbon double bonds in the feedstock. Method 3 also requires a two stage reactor for the ozonolysis reaction. Ozonolysis is performed in a solvent.

Figure 6:
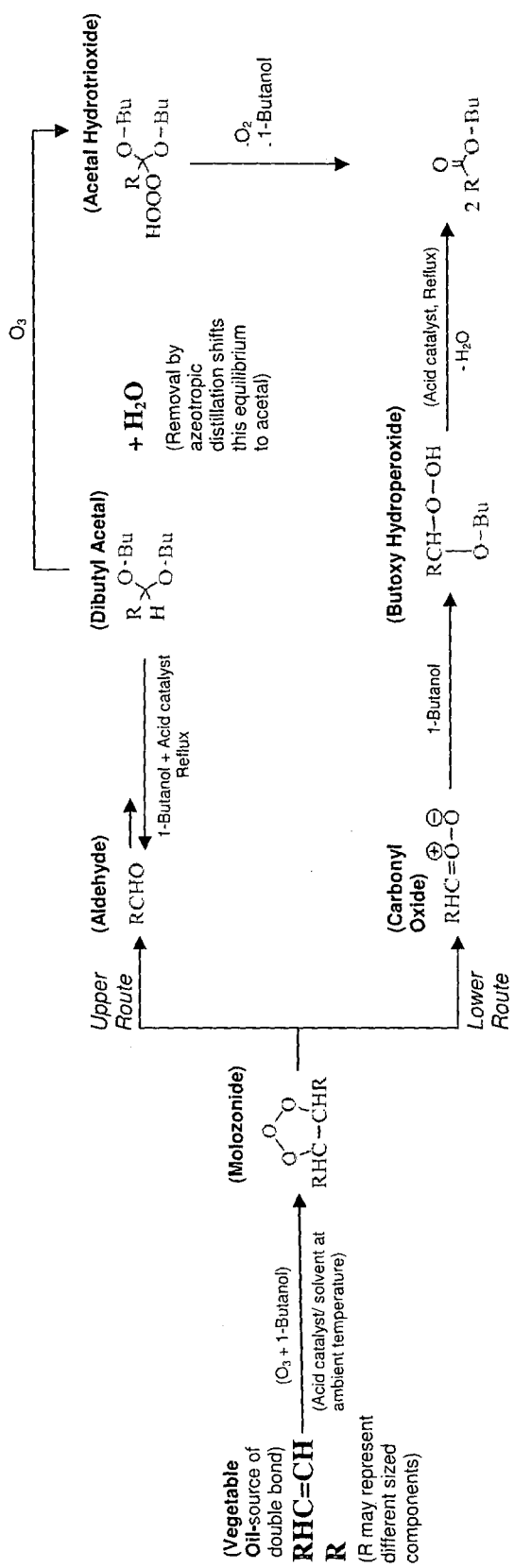
FIG. 6 is a schematic depicting the steps of a two-stage ozonolysis of a substance having a carbon-to-carbon double bond (e.g., vegetable oil) in the presence of 1-butanol (a monoalcohol that azeotropes with water). It is also shown that reflux is carried out before adding the second mole of ozone to maximize conversion of aldehyde functionality to acetal functionality to enhance effective production of butyl esters via more effective formation of acetal hydrotrioxides.

As shown in FIG. 6, Method 3 of the present invention comprises reacting a feedstock such as vegetable oil, for example, with at least one first mole of ozone in the presence of an acidic catalyst and solvent. Any suitable biobased or non-biobased material having at least one substance with at least one carbon-to-carbon double bond can represent the starting material and may be used interchangeably. The biobased material having at least one substance with at least one carbon-to-carbon double bond is represented by RHC=CHR where the R groups may represent different sized components. In the upper route, after refluxing, the resulting acetal reacts with at least one second mole of ozone.

According to a particular aspect, as shown in FIG. 6, the Method 3 further comprises reacting the feedstock with at least one first mole of ozone and at least one second mole of ozone, and further comprises refluxing the acetal before the addition of the second mole of ozone. One of the differences between the conventional method described in the WO2007027223 and the present invention is that refluxing is carried out only after the second mole of ozone is added in WO2007027223.

Further, Method 3 according to the present invention comprises refluxing and removing water by azeotropic distillation, before the addition of the second mole of ozone as shown in the upper route of FIG. 6.

As illustrated in FIG. 6, refluxing before the addition of the second mole of ozone: (1) shifts the aldehyde/acetal equilibrium to the acetal side, (2) partially esterifies all of the carboxylic acid functionality with the monoalcohol (e.g., 1-butanol), and (3) converts butoxy hydroperoxides (the other half of the reaction pathway shown in the lower route) to butyl esters by eliminating water.

In particular, the step of refluxing, before the addition of the second mole of ozone, may further comprise any means, apparatus, methods, and/or techniques to separate water from the condensed distillate obtained by azeotropic distillation. Azeotropic distillation in the present invention may include separating an azeotrope composition by distillation. For example, an azeotropic distillation may include the technique of adding another component to generate a new, lower-boiling azeotrope that is heterogeneous (i.e., producing two, immiscible liquid phases, such as, water and the condensed distillate).

For example, the step of refluxing before the addition of the second mole of ozone includes, but is not limited to, the use of a Barrett or Dean-Stark apparatus to separate water from the condensed distillate obtained by azeotropic distillation. More specifically, refluxing is carried out after all of the double bonds have been consumed by ozone in the present invention.

Method 3 according to the present invention may be carried out in the presence of at least one suitable solvent. For example, suitable solvent(s) described in WO2007027223, which are herein incorporated by reference may be used.

According to a particular aspect, in Method 3 according to the present invention, the monoalcohol may be used in the presence of at least one solvent that azeotropes with water (also referred to as an auxiliary solvent). In particular, the method comprises the addition of at least a first mole and a second mole of ozone, and further comprises refluxing in the presence of at least one solvent that azeotropes with water, before addition of the second mole of ozone.

In particular, the monoalcohol may be a water-soluble lower alcohol, which is miscible with water in all proportions and may be used in the presence of the auxiliary solvent. A water soluble lower alcohol is defined herein the present invention as a monoalcohol with less than four carbon atoms. Examples of water-soluble lower alcohols include, but are not limited to, 1-propanol, 2-propanol, ethanol and methanol.

In particular, the solvent that azeotropes with water is selected from ethyl acetate, methyl acetate, ethyl propionate, methyl propionate, ethyl butyrate, methyl butyrate, ethyl isobutyrate, butyl acetate, butyl butyrate, isobutyl isobutyrate, or a mixture thereof.

Preferably, solvents that azeotrope with water that generate azeotrope distillate compositions have relatively high water compositions. Further, it is preferred that water is essentially insoluble in the solvent/water azeotrope composition after condensation. These combined properties allow for the efficient removal of water present after initial ozone breakthrough by refluxing the reaction mixture and separating the water from solvent in the condensate, for example, when using simple equipment such as a Barrett or Dean Stark apparatus. Ozone breakthrough corresponds to the oxidation of all available carbon double bonds.

According to an aspect of the present invention, refluxing is carried out after the first ozone breakthrough (i.e., after consumption of all double bonds is complete) is observed, for the specific purpose of removing water from the reaction mixture to shift the aldehyde plus monoalcohol to form an acyclic acetal plus water equilibrium toward the acetal side. Therefore, Method 3 is distinct from conventional methods because when monoalcohols are used in the presence of a solvent, ozone is added until an initial ozone breakthrough and the consumption of all double bonds is complete. Then, the second mole of ozone is added to convert any acetals present to ester functionality by reacting with monoalcohols. However, the absorption of the second mole of ozone is inefficient in the case of monoalcohols since only a small percentage of aldehyde functionality generated by the absorption of the first mole of ozone is converted to acyclic acetal functionality in conventional methods.

Tables C and D describes the properties of rigid foam, coatings, and lubricant base polyols obtained from the Method 3 have performance properties that were comparable to those observed in target polyols. The rigid foam derived from Polyol 5 using Method 3 performed similar to the foam obtained from target polyol 17. Also, the flexible foam derived from Polyol 4 has properties similar to those obtained from Polyol 18, but with a significantly higher resilience.

TABLE C

Properties of Rigid Foams Obtained from Fractionated PFAD Polyols
Properties of Rigid Foams Obtained from Fractionated PFAD Polyols

| Sample | Polyol Method | | | | | | | | | | |
|---|---|---|---|---|---|---|---|---|---|---|---|
| | None | 2 | 2 | 2 | 2 | Hybrid | Hybrid | 1 | 1 | 1 | 1 |
| Jeffol SG 360 Ref. Standard (HV 360) | 100 | 0 | 0 | 0 | 0 | 0 | 0 | 0 | 0 | 0 | 0 |
| 52781-17-33 (HV 354) | 0 | 100 | 80 | 0 | 0 | 0 | 0 | 0 | 0 | 0 | 0 |
| 52781-101-28 (HV 316) | 0 | 0 | 0 | 100 | 80 | 0 | 0 | 0 | 0 | 0 | 0 |
| 52781-95-33 (HV 392) | 0 | 0 | 0 | 0 | 0 | 100 | 80 | 0 | 0 | 0 | 0 |
| 52921-5-22 (HV 300) | 0 | 0 | 0 | 0 | 0 | 0 | 0 | 100 | 80 | 0 | 0 |
| 52781-73-29 (HV 360) | 0 | 0 | 0 | 0 | 0 | 0 | 0 | 0 | 0 | 100 | 80 |
| Glycerol | 0 | 0 | 20 | 0 | 20 | 0 | 20 | 0 | 20 | 0 | 20 |
| % Battelle Polyol | 0 | 100 | 100 | 100 | 100 | 100 | 100 | 100 | 100 | 100 | 100 |
| Isocyanate Index | 1.05 | 1.05 | 1.05 | 1.05 | 1.05 | 1.05 | 1.05 | 1.05 | 1.05 | 1.05 | 1.05 |
| Rise time, sec | 125 | 120 | 130 | 85 | 135 | 71 | 110 | 80 | 126 | 105 | 115 |
| Free-rise density, pcf | 2.20 | 2.40 | 2.30 | 2.27 | 2.04 | 2.20 | 2.20 | 2.15 | 2.20 | 2.30 | 2.17 |
| Comments | Slight Shrinkage at 120 C. | Significant Shrinkage at 120 C. | No Shrinkage at 120 C. | Slight Shrinkage at 120 C. | No Shrinkage at 120 C. | No Shrinkage at 120 C. | No Shrinkage at 120 C. | Shrinkage at 120 C. | No Shrinkage at 120 C. | Shrinkage at 120 C. | No Shrinkage at 120 C. |
| Compressive Strength @ Yield, psi | 26.7 ± 2.0 | 32.8 ± 4.8 | 36.5 ± 2.6 | 28.1 ± 1.8 | 21.4 ± 0.3 | 28.0 ± 3.9 | 29.3 ± 2.1 | 22.6 ± 6.1 | 29.7 ± 4.1 | 30 ± 0 | 30.9 ± 2.5 |
| Compressive Strain @ Yield, psi | 5.1 ± 0.1 | 5.8 ± 1.6 | 5.2 ± 0.9 | 4.8 ± 0.5 | 4.9 ± 0.3 | 4.8 ± 0.2 | 5.3 ± 0.2 | 5.0 ± 0.2 | 6.3 ± 2.6 | 4.8 ± 0.7 | 4.7 ± 0.3 |
| Origin | Standard petroleum polyol | Target polyol prepared by Method 2 | | Transesterified from flexible foam polyol 52781-94-33 | | Transesterified from butyl esters | | Esterified/ transesterified from "polyacid" 52781-107-5 | | "Repaired" Method 1 rigid foam polyol after initial aqueous extraction | |

TABLE D

Rigid Foam, Coatings, and Lubricant Base Polyols Prepared from Fractionated PFAD Butyl Esters Using Method 3

| | Rigid Foam Polyol | | Coatings Polyol | | Lubricant Base Polyol | |
|---|---|---|---|---|---|---|
| | Target | Obtained Polyol | Target | Obtained Polyol | Target | Obtained Polyol |
| LRB | 52781-17-33 | 52781-95-33 | 52781-22-28 | 52781-113-24 | 52781-111-26 | 52921-1-23 |
| HV | 354 | 392 | 231 | 268.8 | 52.4 | 56.9 |
| AV | 0.9 | 0.0 | 0.0 | 0.0 | 0.0 | 0.0 |

The Master Batch Approach Applied to Ester Polyols Produced by Repairing Polyacids Method 2 ester polyols had been converted to high performance rigid foams and moderate performance flexible foams and served as targets for head-to-head comparison with the polyols of Method 1. Method 2 polyol 5278 1-17-33 (polyol 17), which was derived from fractioned PFAD was converted into a high quality rigid foam and thus served as a target for preparation by the Master Batch Approach applied to Method 1.

This Method 2 ester polyol had been prepared using a 2.5 hydroxyl/carboxyl ratio and incorporated sorbitol and glycerin to provide crosslinking and Me-PG to provide resistance to phase separation.

Preparation of the Method 1 version of this ester polyol was performed by incorporating the same reagents except that fractionated PFAD was pre-esterified with sorbitol (required to provide solvent solubility) and a 2.5 hydroxyl/reactive site ratio was used. Ozonolysis was performed using sulfuric acid and subjected to aqueous basic washing to remove sulfuric acid after ozonolysis. However, a relatively low yield was observed and NMR analysis showed that the washing procedure had apparently removed a significant portion of starting glycerin and Me-PG.

Accordingly, a transesterification reaction was performed with the amount of glycerin and Me-PG that was "missing" to obtain "repaired" polyol 5278 1-73-29 (polyol 73). The hydroxyl value (HV) of this polyol was 360, which compared very favorably to the hydroxyl value (HV) of the target polyol 17 (354). More importantly, when polyol 73 was converted to a rigid foam, its combined properties were shown to quite similar to rigid foam obtained from polyol 17. Performance data for rigid foams obtained from these two ester polyols as well as from other ester polyols are shown in Table C. These results provide confirmation that this transesterification approach can be used to "repair" a deficient ester polyol and improving its properties.

Table E compares the starting material and product polyols obtained from the Master Batch using Methods 1, 2, and 3, and the Modified Method (repairing deficient ester polyols).

TABLE E

A Comparison chart between Ester Polyols obtained by applying the Master Batch Method to products of Methods 1, 2, 3 and the Modified Method

| Method | Polyol No. (starting) | Hydroxyl Value ($HV_1$) | Polyol No. (product) | Hydroxyl Value ($HV_t$) | Percent Increase (%) |
|---|---|---|---|---|---|
| 1 | No. 107 | 14.4 | No. 5 | 300 | 90.8% |
| 1 | No. 107 | 14.4 | No. 4 | 15.8 | 4.64% |
| 2 | No. 94-33 | 56.2 | No. 101 | 316 | 69.8% |
| 2 | | | No. 32-30 | 207 | |
| 3 | No. 17 | 354 | No. 95 | 392 | 5.09% |
| 3 | No. 22 | 231 | No. 113 | 268.8 | 7.56% |
| 3 | No. 57 or 111 | | No. 1 | 56.9 | |
| Mod. 1 | No. 17 | 354 | No. 73 | 360 | |

LIST OF REFERENCES CITED

1. U.S. Pre-Grant Publication No. 2005/0112267 to Yeong et al.
2. "Preparation and Characterization of Trimethylolpropane Esters from Palm Kernel Oil Methyl Esters" to Robiah et al.
3. Malaysian Patent Nol. 140833 to Robiah et al.
4. WO2007027223

The invention claimed is:

1. A method for producing an ester polyol, comprising:
   transesterifying a first ester polyol with a primary polyol to produce a second ester polyol, wherein a hydroxyl value (HV) of the second ester polyol is greater than a hydroxyl value ($HV_t$) of the first ester polyol and the first ester polyol is prepared by the sequential steps of:
   reacting a fatty acid distillate with ozone in the presence of a reactant and a catalyst to produce a reaction mixture, wherein the ozone comprises at least two moles of ozone per carbon-to-carbon double bond of the fatty acid distillate; and
   refluxing the reaction mixture to produce the first ester polyol having a hydroxyl value ($HV_t$).

2. The method according to claim 1, wherein the reactant is a polyol.

3. The method according to claim 2, wherein the reacting is carried out in the presence of a solvent selected from the group consisting of ethyl acetate, methyl acetate, ethyl propionate, methyl propionate, ethyl butyrate, methyl butyrate, ethyl isobutyrate, butyl acetate, butyl butyrate, isobutyl isobutyrate, and a mixture thereof.

4. The method according to claim 1, wherein the catalyst is an acid catalyst.

5. The method according to claim 1, wherein the hydroxyl value of the second ester polyol is greater than about 300.

6. A method for producing an ester polyol, comprising:
   transesterifying a first ester polyol with a primary polyol to produce a second ester polyol, wherein a hydroxyl value (HV) of the second ester polyol is greater than a hydroxyl value ($HV_t$) of the first ester polyol and the first ester polyol is prepared by the sequential steps of:
   hydrolyzing a triglyceride to produce a mixture of fatty acids;
   esterifying the mixture of fatty acids with at least one monoalcohol to form at least one fatty acid alkyl ester;
   performing fractionation by distillation of the at least one fatty alkyl acid ester to partially remove saturates resulting in at least on fractionated fatty alkyl acid ester;
   reacting the at least one fractionated fatty alkyl acid ester with ozone to produce a mixture of ozone esters, wherein the ozone comprises one mole of ozone per carbon-to-carbon double bond of the at least one fractionated fatty alkyl acid ester; and
   transesterifying the mixture of ozone esters with a primary polyol to produce the first ester polyol having a hydroxyl value ($HV_t$).

7. The method according to claim 6, wherein the at least one monoalcohol comprises 1-butanol or isomers thereof, 1-pentanol or isomers thereof, 1-hexanol or isomers thereof, 1-heptanol or isomers thereof, 1-octanol or isomers thereof, 1-nonanol or isomers thereof, 1-decanol or isomers thereof, 1-undecanol or isomers thereof, 1-dodecanol or isomers thereof, 1-tridecanol or isomers thereof, 1-tetradecanol or isomers thereof, cetyl alcohol or isomers thereof, or stearyl alcohol or isomers thereof.

8. The method according to claim 7, wherein the at least one monoalcohol is methanol, 1-butanol, or 1-hexanol.

9. The method according to claim 8, wherein the hydroxyl value of the second ester polyol is greater than about 316.

10. The method according to claim 8, wherein an acid value (AV) of the second ester polyol is less than about 0.9.

11. A method for producing an ester polyol, comprising:
    transesterifying a first ester polyol with a primary polyol to produce a second ester polyol, wherein a hydroxyl value (HV) of the second ester polyol is greater than a hydroxyl value ($HV_t$) of the first ester polyol and the first ester polyol is prepared by the sequential steps of:
    reacting a substance having at least one carbon-to-carbon double bond with ozone in the presence of at least one monoalcohol that azeotropes with water and at least one solvent to produce a plurality of ozone esters, wherein the ozone comprises at least one first mole of ozone and at least one second mole of ozone and wherein the reacting step comprises refluxing the substance having the at least one carbon-to-carbon double bond to remove water before adding the second mole of ozone; and
    transesterifying the plurality of ozone esters with a primary polyol to produce the first ester polyol having a hydroxyl value ($HV_t$).

12. The method according to claim 11, wherein the at least one solvent comprises at least one solvent that azeotropes with water.

13. The method according to claim 11, wherein the reacting step further comprises an acid catalyst.

14. The method according to claim 12, wherein the at least one solvent that azeotropes with water is selected from the group consisting of ethyl acetate, methyl acetate, ethyl propionate, methyl propionate, ethyl butyrate, methyl butyrate, ethyl isobutyrate, butyl acetate, butyl butyrate, isobutyl isobutyrate, and a mixture thereof.

15. The method according to claim 11, wherein the at least one monoalcohol that azeotropes with water comprises at least one monoalcohol with at least four carbon atoms.

16. The method according to claim 11, wherein the at least one monoalcohol that azeotropes with water comprises 1-butanol or isomers thereof, 1-pentanol or isomers thereof, 1-hexanol or isomers thereof, 1-heptanol or isomers thereof, 1-octanol or isomers thereof, 1-nonanol or isomers thereof, 1-decanol or isomers thereof, 1-undecanol or isomers thereof, 1-dodecanol or isomers thereof, 1-tridecanol or isomers thereof, 1-tetradecanol or isomers thereof, cetyl alcohol or isomers thereof, or stearyl alcohol or isomers thereof.

17. The method according to claim 11, wherein the at least one monoalcohol that azeotropes with water to form an azeotrope composition, and the azeotrope composition has a water content from a range of 4 to 90 percent water.

18. The method according of claim 11, wherein the reacting step comprises reacting the substance having at least one carbon-to-carbon double bond in the presence of an ozonolysis catalyst.

19. The method according to claim 11, wherein the substance having at least one carbon-to-carbon double bond comprises a vegetable oil, animal fat, or a mixture thereof.

20. The method according to claim 11, wherein the substance having at least one carbon-to-carbon double bond comprises a fatty acid.

21. The method according to claim 1, wherein the primary polyol is selected from the group consisting of glycerin, trimethylolpropane, pentaerythritol, 1,2-propylene glycol, 1,3-propylene glycol, 2-methyl-1,3-propanediol, 1,4-butanediol, ethylene glycol, aldoses, ketoses, alditols, disaccharides, and combinations thereof.

22. The method according to claim 21, wherein:
when present, the aldose is glucose; and/or
when present, the ketose is fructose; and/or
when present, the alditol is glucitol; and/or
when present, the disaccharide is sucrose.

23. The method according to claim 6, wherein the primary polyol is selected from the group consisting of glycerin, trimethylolpropane, pentaerythritol, 1,2-propylene glycol, 1,3-propylene glycol, 2-methyl-1,3-propanediol, 1,4-butanediol, ethylene glycol, aldoses, ketoses, alditols, disaccharides, and combinations thereof.

24. The method according to claim 23, wherein:
when present, the aldose is glucose; and/or
when present, the ketose is fructose; and/or
when present, the alditol is glucitol; and/or
when present, the disaccharide is sucrose.

25. The method according to claim 11, wherein the primary polyol is selected from the group consisting of glycerin, trimethylolpropane, pentaerythritol, 1,2-propylene glycol, 1,3-propylene glycol, 2-methyl-1,3-propanediol, 1,4-butanediol, ethylene glycol, aldoses, ketoses, alditols, disaccharides, and combinations thereof.

26. The method according to claim 25, wherein:
when present, the aldose is glucose; and/or
when present, the ketose is fructose; and/or
when present, the alditol is glucitol; and/or
when present, the disaccharide is sucrose.

* * * * *